United States Patent [19]

Staub

[11] 4,359,052

[45] Nov. 16, 1982

[54] REMOVABLE TIP CAUTERY

[75] Inventor: David E. Staub, Clearwater, Fla.

[73] Assignee: Concept Inc., Clearwater, Fla.

[21] Appl. No.: 895,625

[22] Filed: Apr. 12, 1978

Related U.S. Application Data

[63] Continuation of Ser. No. 652,422, Jan. 26, 1976, abandoned.

[51] Int. Cl.³ .............................................. A61B 17/38
[52] U.S. Cl. ................................. 128/303.1; 206/363; 219/233
[58] Field of Search ........... 128/303.1, 303.13, 303.14, 128/303.17, 303.18, 303 R, 405, 350 R, 214.4, 800, 801; 219/233; 206/210, 229, 361, 363–365; 21/82 R, 82 H

[56] References Cited

U.S. PATENT DOCUMENTS

| | | | |
|---|---|---|---|
| 1,814,791 | 7/1931 | Ende | 128/303.18 X |
| 2,611,365 | 9/1952 | Rubens | 128/303.13 |
| 2,949,107 | 8/1960 | Ziegler | 128/303.13 X |
| 3,295,514 | 1/1967 | Hein et al. | 128/303.14 X |
| 3,335,723 | 8/1967 | Waldman, Jr. | 206/365 X |
| 3,533,397 | 10/1970 | Scher | 128/405 X |
| 3,558,854 | 1/1971 | Siegel et al. | 128/303.14 X |
| 3,757,771 | 9/1973 | Ruegg et al. | 128/214.4 X |
| 3,898,993 | 8/1975 | Taniguchi | 128/350 R |
| 3,978,312 | 8/1976 | Barton et al. | 128/303.14 X |

FOREIGN PATENT DOCUMENTS

| | | | |
|---|---|---|---|
| 668561 | 8/1965 | Belgium | 219/233 |
| 564175 | 12/1923 | France | 219/233 |

*Primary Examiner*—Lee S. Cohen
*Attorney, Agent, or Firm*—Gipple & Hale

[57] ABSTRACT

A variable temperature cautery comprising a housing configured to retain a voltage source with an adaptor plug and associated heating tip assembly in operative relation to each other. A control assembly is movably attached to the housing to operatively couple a conductor disposed within the housing and the voltage source. The conductor is movable into and out of operative engagement with the adaptor plug by an actuator mechanism to selectively deliver an infinite variety of voltages to the removable heating tip assembly of the cautery. The housing or handle of the cautery is encapsulated and sterilized by placing it in a sterile bag device. A disposable tip assembly is used in conjunction with the cautery handle and covering bag and is provided with sharpened electrode leads which puncture the bag and fit into the instrument handle so that current can flow to the wire loop cutting area to provide a hot cutting tip.

5 Claims, 12 Drawing Figures

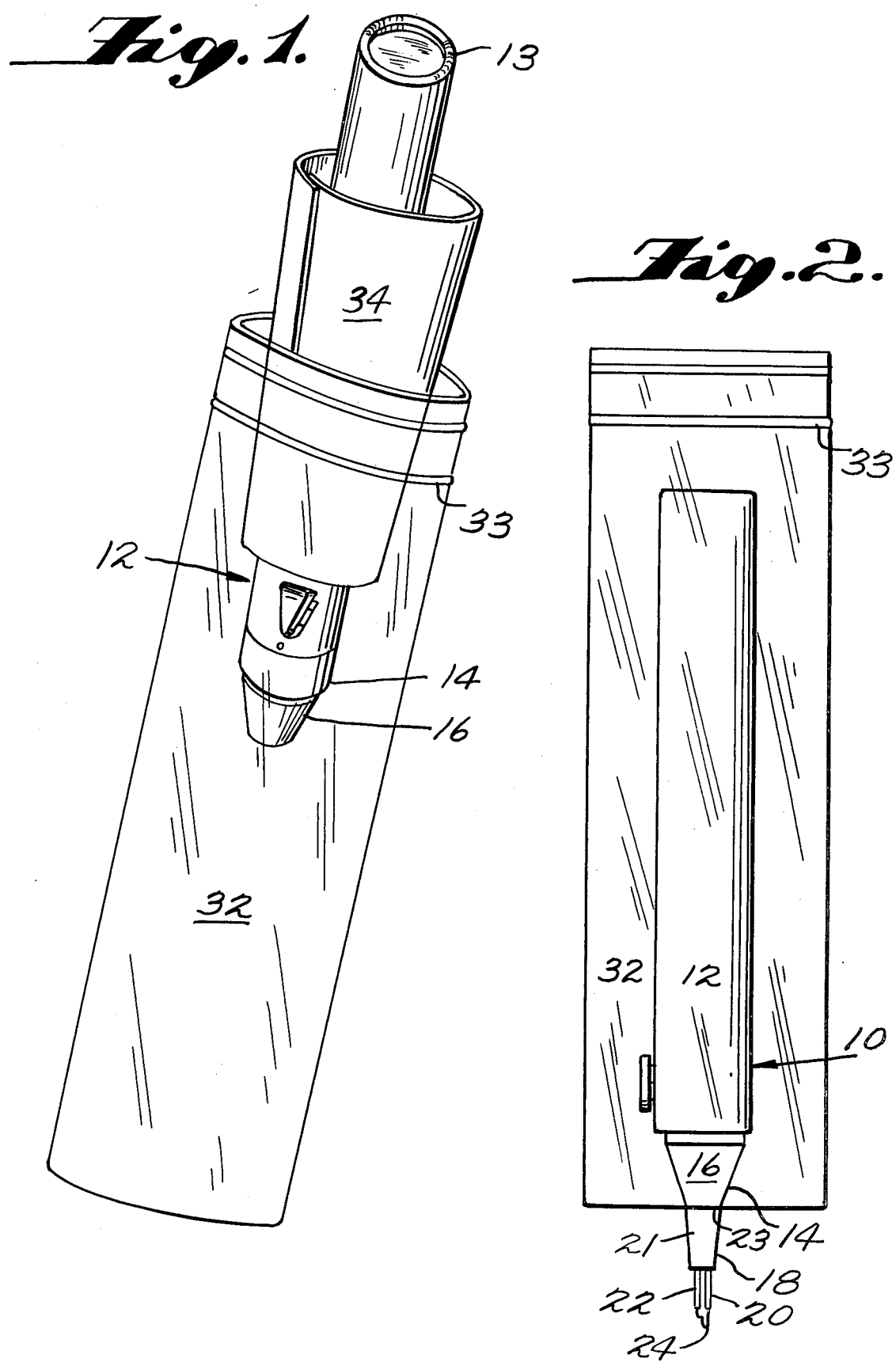

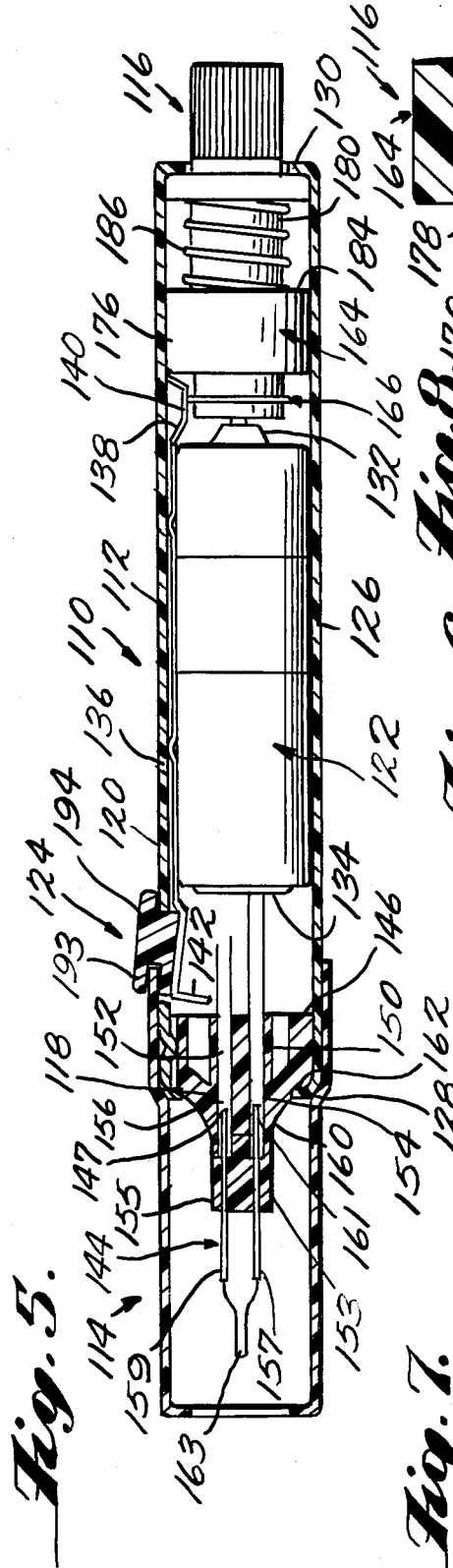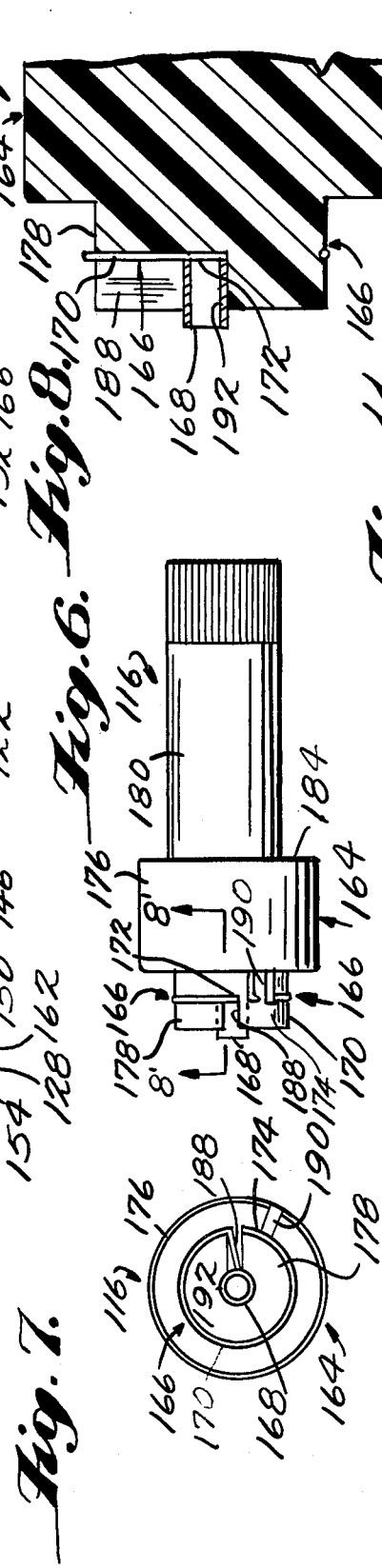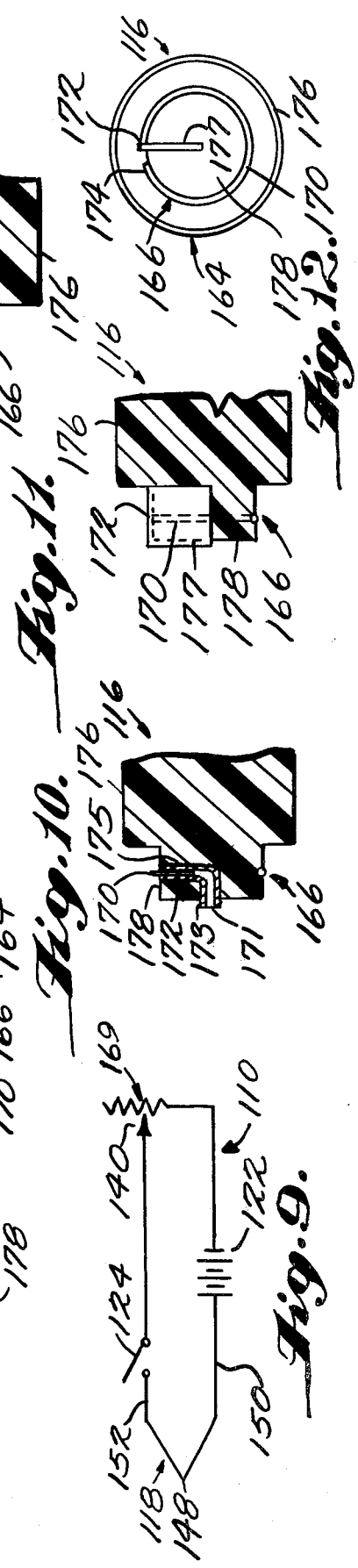

REMOVABLE TIP CAUTERY

This is a continuation of application Ser. No. 652,422 filed Jan. 26, 1976, now abandoned.

BACKGROUND OF THE INVENTION

The present invention generally relates to a cautery device and more particularly pertains to a battery operated removable tip cautery.

Many types of portable battery operated cautery instruments have been developed and used, one of which is described in U.S. Pat. No. 3,613,682. These battery operated cautery instruments are used on the basic principle that after each surgical use the entire instrument is disposed of. However, it has been found that the actual use life of such cauteries is much greater than the time required for a single surgical use so that the cautery could be used for other surgical proceedings if a way could be found to sterilize the instrument for additional surgical usage. Such sterilization generally requires autoclaving or other associated heat treating of the instrument which treatment has been found to destroy or damage the batteries in the instrument. Another means of sterilization is accomplished through the use of ethylene oxide gas. While this treatment does not damage the batteries in the instrument, small hospitals or health treatment facilities are not provided with the necessary gas treatment apparatus. Another problem inherent with the use of this type of gas treatment is that aluminum components cannot be used in the instrument due to the interaction of the gas and the aluminum which decreases the sterilization capability of the gas and builds up salt on the aluminum.

DESCRIPTION OF THE PRIOR ART

A reusable battery operated cautery is described in U.S. Pat. No. 3,461,874. This cautery uses a plug in cautery tip assembly which is removed and stored in the bore of a charger stand when the handle assembly is being recharged. It should be noted that the cautery must be sterilized in the previously discussed manner.

The present invention differs from the previously identified cautery in that it uses an encapsulated instrument handle which is sterilized through the use of a novel sterile bag device. A disposable tip assembly is used in conjunction with the cautery instrument and covering bag and is provided with sharpened electrode leads which puncture the bag and fit into the instrument handle so that current can flow to the wire loop cutting area to provide a hot cutting tip.

SUMMARY OF THE INVENTION

This invention relates to a hand-held variable temperature cautery. More specifically, the variable temperature cautery comprises a housing configured to retain a voltage source with an adaptor plug and associated heating tip assembly in operative relation to each other. In addition, a control means is movably attached to the housing to operatively couple a conductor means disposed within the housing and the voltage source. The conductor means is movable into and out of operative engagement with the adaptor plug by an actuator means to operate the cautery as more fully described hereinafter.

One feature of the subject invention includes the ability to selectively deliver an infinite variety of voltages to the removable heating tip assembly of the cautery. This selectivity of temperature variations determined by the user of the cautery depends upon the particular applications for which the cautery is being utilized.

The housing, a hollow substantially cylindrical barrel, is preferably formed of a dielectric material such as polyvinyl or other applicable substance capable of withstanding relatively abusive treatment during use. The barrel retaining means is formed at each end to retain the adaptor plug and control means in opposite ends thereof. Disposed within the barrel is the conductor means which comprises a strip of conductive material extending substantially the length of the barrel.

A heating tip assembly comprises a heater element and mounting plug. The mounting plug is configured to connect the heater element to the adaptor plug in operative relation to the conductor strip and voltage source.

The control means comprises an adjustment means and a second conductor means attached thereto rotatably attached to the opposite end of the barrel. The second conductor means comprises an origin and terminus interconnected by a continuous conductor element. The control means is disposed relative to the first conductor means so that the position of the adjustment means relative to the first conductor means determines the voltage value applied to the heater tip assembly.

In operation, the operator initially determines the output voltage required for a particular application. The operator then adjusts the cautery to deliver this preselected output by rotating the control means relative to the barrel. A visual indication of the output selected may be indicated by means of aligning an index mark formed on the exterior of the control means with a scale printed around the exterior of the barrel. Having selected the desired output, the operator next places the barrel in a sterile flexible bag and mounts the heater tip assembly to the adapter plug through the flexible bag with the barrel being contained in the bag. The operator then moves the actuator to the second or "on" position to complete the circuit between the voltage source and heater tip assembly causing the heater element to heat up. Once heated, the heater element may be touched to exposed wounds or cuts to clean and heal the wounds or remove sutures and the like. In this manner the previously determined voltage limits of proper value are provided.

It can thus be seen that by virtue of the invention, a single device can be set to selectively deliver a variety of outputs. The housing device can also be used several times in a sterile condition before it is disposed of. The structure as contained is simple, safe, economical to manufacture and easy to use in any variety of field conditions.

The construction, operation and advantages of the invention will become more readily apparent and understood from the following detailed specification accompanying the drawings in which:

BRIEF DESCRIPTION OF THE DRAWINGS

FIG. 1 is a perspective view of the cautery body being placed into a protective bag;

FIG. 2 is a side elevational view of the cautery body of FIG. 1 placed in a protective bag with the tip assembly mounted to the body;

FIG. 5 is a cross-sectional side elevational view of a variable temperature cautery embodiment of the invention;

FIG. 6 is an enlarged side view of the control means of FIG. 5;

FIG. 7 is an end view of the control means of FIG. 6;

FIG. 8 is an enlarged partial cross-sectional side view of the control means taken along line 8'—8' of FIG. 6;

FIG. 9 is an electrical schematic of the variable temperature cautery;

FIG. 10 is a sectional view showing another embodiment of the control means of the present invention;

FIG. 11 is a cross-sectional view showing yet another embodiment of the control means of the present invention; and FIG. 12 is an end view of the embodiment shown in FIG. 11.

Similar reference characters refer to similar parts throughout the several views of the drawings.

DETAILED DESCRIPTION OF THE DRAWINGS

Figures 3, 4:
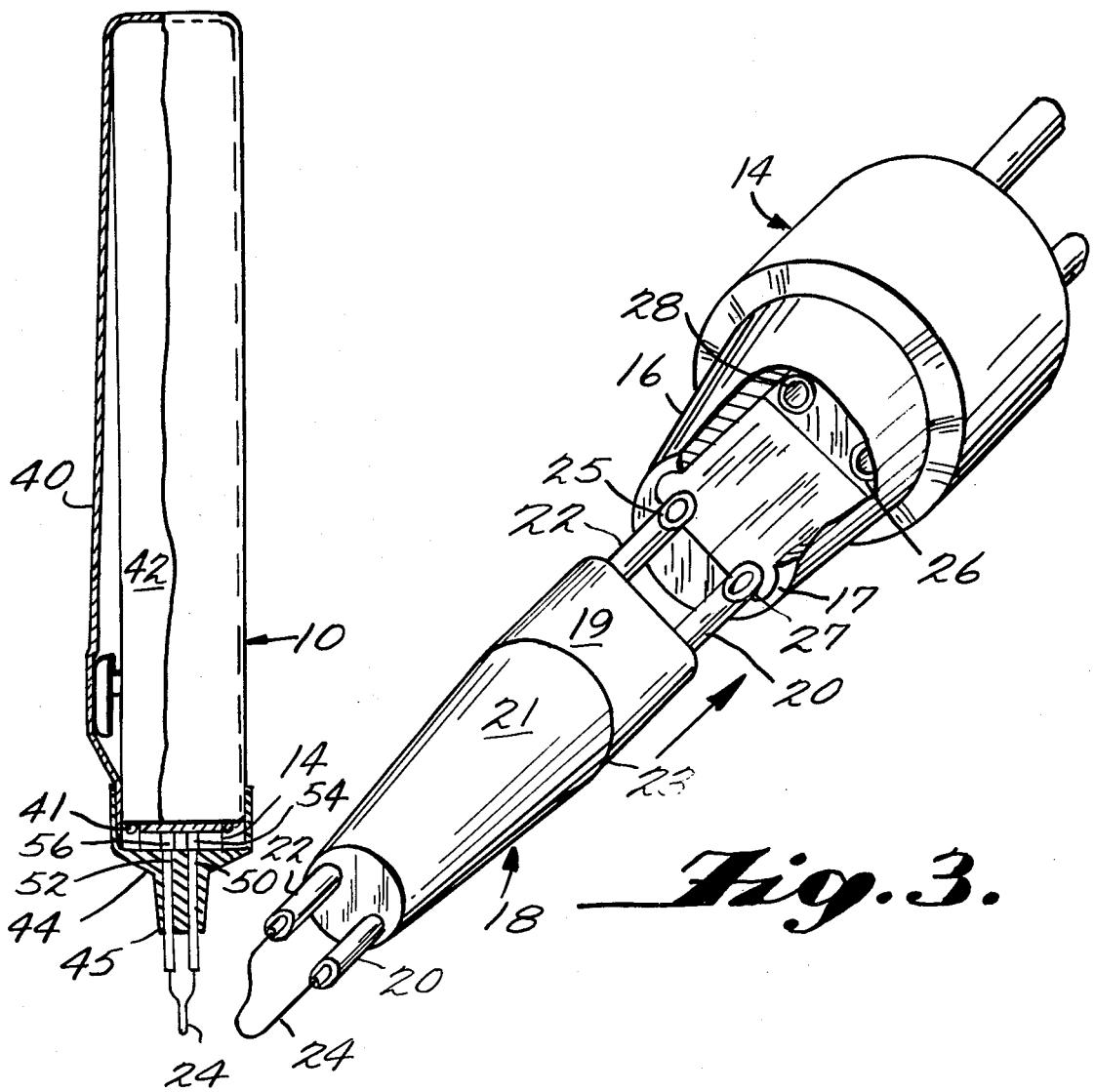
FIG. 3 is an exploded enlarged perspective view of the tip assembly and adaptor plug partially in section of the cautery instrument shown in FIG. 2.
FIG. 4 is a side elevational view partially in section of another embodiment of the invention.

In the invention as shown in FIGS. 1-12 the novel cautery 10 comprises a barrel or handle assembly 12 formed by a tubular plastic case 13 in which is mounted an adaptor plug assembly 14. The adaptor plug assembly 14 comprises a frustum-conical body 16 which extends past the end of the tubular handle assembly and is constructed to hold a heater tip assembly 18 which fits into the adaptor plug body 16.

The heater tip assembly 18 comprises a plastic plug body 21 having hollow electrode leads 20 and 22 extending therefrom, the forward ends of which are secured to a wire loop heater element 24 of platinum or other similar resistance wire. The wire element 24 is secured to the leads by welding or preferably crimping the ends of the hollow leads down upon the wire loop heater element to secure the wire loop element in place. The leads 20 and 22 extend through the plug 18 and extend on the distal side outward a predetermined distance which is sufficient to fit into hollow electrode leads 26 and 28 which are secured in the adaptor plug body. These leads extend through plug body 16 and terminate at the bottom of an oval shaped blind bore 17 formed in the plug body. The heater tip assembly is formed with a male portion 19 which is substantially ovally shaped and adapted to seat and snugly fit in the oval shaped bore 17 cut in the adaptor plug body 16.

It is apparent that the bore can take any desired shape and the tip assembly male portion any compatable companion shape. The heater tip assembly body 21 has a frustum-conical shape from which the oval cylindrical male end portion 19 extends. Planar surface 23 of the body 21 acts as a stop against the top surface 25 of adaptor plug 16 thus limiting the distance that the heater tip assembly 18 can be inserted into the bore 17 of the plug 16. The distal ends 27 of the leads 20 and 22 extend into the hollow electrode leads 26 and 28 of the adaptor plug body when the male portion 19 is inserted into bore 17 to form an electrical connection. These distal ends 27 are preferably beveled to form a sharp cutting edge which is used to penetrate a flexible plastic bag 32 into which the cautery handle or barrel 12 is dropped.

The flexible plastic bag 32 preferably is provided with a sealed closed end and an open opposite end which is adapted to be sealed in a conventional manner through a press fit, tongue and groove type seal 33 which is known in the art under the trade name "ZIPLOC." Bag 32 is provided with an internal funnel 34 of paper or other suitable meaterial which is preferably tapered and flexible so that it can be folded into a flat planar configuration and inserted into the bag 32 for convenient packing and storage. In use the sterile bag 32 is pulled out of its pre-sterilized container, the bag seal is broken and pressure is placed on the funnel sleeve 34 causing it to expand into a substantially conical shape thereby causing the interior of the bag 32 to expand allowing for easy entry of the cautery barrel assembly 12 which is dropped through the funnel 34 into the bag. The funnel 34 is then pulled out of the bag and the open end is pressed together so that the tongue and groove configuration snaps shut forming a sealed package holding the cautery barrel or handle in a sterile wrapper.

The heating tip body 21 is then placed against the bag adjacent the end of the adaptor plug 16 and the sharp edges 27 of electrical leads 20 and 22 are pressed against the plastic bag 32 puncturing the package with the heating tip body 21 being seated next to the adaptor plug body 16 but separated by the plastic bag wall. The electrical contacts are made by positioning hollow leads 20 and 22 within the hollow electrode leads 26 and 28 so that the outer surface of leads 20 and 22 engage the inner surface of leads 26 and 28. The cautery and associated batteries contained therein are described and incorporated in this application by reference as is shown and described in U.S. Pat. No. 3,613,682 issued Oct. 19, 1971.

An alternate embodiment of the invention is shown in FIG. 4 in which a flexible rubber baggie 40 having an O-ring 41 on one end is placed over the cautery body 42 so that a cap 44 and associated heating wire assembly 45 can be placed over the cautery body and baggie 40 with the electrode leads 50 and 52 of the cap fitting into similarly situated hollow leads 54 and 56 in the cautery adaptor plug. The O-ring 41 of the baggie forms a seal so that after surgery has been performed, the heating cap assembly 44 and the outer covering baggie 40 can be removed. A new flexible bag is then placed on the body with a new heating cap assembly mounted so that the cautery can again be used for additional cutting or cauterizing.

In the preferred embodiment the temperature of the cautery loop can be varied to obtain the desired cutting temperature.

As shown in FIG. 5, this preferred embodiment of the invention relates to a hand-held variable temperature cautery indicated as 110 comprising a housing 112 and protective cap 114 removably attached thereto. In the cautery 110 control means 116 and adaptor means 118 are attached to opposite ends of housing 112, a first conductor means 120 and a voltage source 122 operatively retained within housing 112, and an actuator means 124 is provided outside of the housing.

The housing 112 comprises a hollow substantially cylindrical barrel 126 including retaining means comprising a pair of retainer lips 128 and 130 formed on its upper and lower ends in a substantially annular configuration. The barrel 126 is preferably formed of dielectric material such as polyvinyl or other similar or applicable substance providing the desired characteristics including the ability to withstand relatively abusive treatment during use. The barrel 126 is internally insulated. Retainer lips 128 and 130 are configured to operatively couple the adaptor means 118 and control means 116 respectively to the barrel 126. A terminal 132 of the voltage source 122 in the form of a battery engages control means 116 while the opposite terminal 134 of battery 122 engages adaptor means 118. If desired, a plurality of batteries or other voltage sources may be placed in series or parallel, end to end to increase the available voltage output. The first conductor means 120 comprises an elongated strip 136 of conductive material which extends substantially the length of the barrel 126. At least one portion 138 of the strip 136 includes a first contact means or wiper 140 positioned to operatively engage control means 116 while a second portion includes a second contact means 142 shaped to operatively engage the adaptor means 118.

The adaptor means 118 comprises a housing 146 with electrodes 150 and 152 extending through channels 154 and 156 respectively formed in the housing 146 into the interior of the barrel 126. The inner end of the first electrode 150 is disposed to engage the terminal 134 of battery 122 while the second electrode 152 is spaced apart from the terminal 134.

The outer ends of electrodes 150 and 152 terminate at the seat of a blind bore 147 cut into housing 146. A heating tip assembly 153 is designed to be seated in the blind bore 147 so that the tip assembly can be removably mounted to adaptor plug. The heating tip assembly 153 includes a tip body 155 which holds two through-going electrodes 157 and 159 and a wire tip 163 interconnected between the third electrode 157 and the fourth electrode 159.

The third and fourth electrodes 157 and 159 are tubular in shape and of smaller diameter than the first and second electrodes 150 and 152 and are adapted to be inserted into the first and second electrodes to provide an electrical connection. The ends 161 of electrodes 157 and 159 opposite the wire tip 163 are beveled to form a sharp cutting surface.

The mounting housing 146 comprises an enlarged base 158 and a reduced upper portion 160 which together cooperatively form a ledge 162 therebetween. The ledge 162 and retaining lip 128 engage each other to secure the adaptor means 118 to the barrel 126. As configured, the adaptor means 118 comprises an integral unit which prevents any accidental separation of parts during use.

An alternate embodiment of the present invention may include the integral adaptor means 118 being welded or similarly attached to casing 112.

As shown by FIGS. 6 through 8, the control means 116 comprises an adjustment 164 and a second conductor means 166. The second conductor means 166 comprises a hollow substantially cylindrical member 168 and a conductive wire-like strip 170 coupled thereto. The strip 170 comprises an origin 172 and terminal point 174. Adjustment means 164 comprises an enlarged base 176 having oppositely disposed inner portions 178 and 180 extending outwardly from the opposite sides of base 176. The intersection of base 176 and portion 180 cooperatively forms ledge 184 which engages bias means 186 to hold the voltage source 122 in engagement with the first electrode 150. Inner portion 178 includes channel 188 for accommodating the junction of origin 172 of strip 170 and cylindrical members 168. Similarly, tab 190 is provided to attach terminal point 174 thereto. Aperture 192 is formed in the tab to secure the terminal contact means cylindrical member 168 to portion 178 in a corresponding relation to terminal 132 of battery 122.

Another embodiment of the invention is disclosed in FIG. 10 and includes a substantially L-shaped element 171. Portion 173 of element 171 may be either solid or hollow as desired. The portion indicated as 175 is specifically configured to allow crimping between portion 175 and the origin 172 of conductive strip 170.

Yet another embodiment of the present invention as shown in FIG. 12 envisions a solid flange 177 fitted on portion 176 of the control means. Conductive strip 170 has its origin 172 also crimped to engage flange 177 as shown in both FIGS. 11 and 12. In the alternative, conductive strip 170 has its origin tack welded or otherwise securely attached thereto to provide efficient electrical contact therebetween. It should also be noted that conductive strip 170 may include any of a number of various configurations and is not intended to be limited to a "flat" or "round" configuration as represented. Irrespective of the embodiment utilized, member or elements 168, 171 and/or 177 are configured and positioned relative to the terminal 132 of battery 122 so as to effect proper, efficient and reliable electric contact therebetween.

As shown in FIG. 5, the actuator means 124 comprises a suitable dielectric material and includes slot 193 formed inwardly from one end thereof. Actuator means 124 thus comprises portion 194 disposed to engage conductor means 120 to move second contact means 142 into electrical contact with the electrode 152. This is accomplished when the cap 114 is removed from the housing 112 and the actuator means 124 is manually depressed.

FIG. 9 represents schematic circuitry of the operation of cautery 110. As shown, when the control means 116 is rotated relative to the housing 112 to vary the voltage supplied to applicator means 118, the voltage 169 varies depending upon the position of contact therebetween and the resulting resistance. Actuator means (switch) 124, when closed completes the circuit passing current through electrodes 150 and 152 to electrodes 157 and 159 on to wire tip 163 which is heated.

Another embodiment of the present invention comprises a conductive strip 170 electrically connected to conductive member or flange 177 at its origin 172. The electrical connection at origin 172 between the conductive strip 170 and flange 177 may be accomplished by tack welding or otherwise attaching the conductive strip to the conductive element or flange 177 by an applicable means sufficient to establish proper and efficient electrical contact.

The opposite or terminal point 174 is attached to portion 178 of adjustment means 174 by means of an integrally formed slot. The slot has its inner wall surface specifically configured to define a projection means therein. This projection means is disposed and configured to engage the terminal point or end 174 of conductive strip 170 in such a manner as to lock the terminal point 174 within the slot and thereby maintain the conductive strip 170 in operative relation relative to the first contact 140 which comprises a portion of the first conductor means.

In operation, the operator initially determines the output voltage required for a particular application. The operator then adjusts the cautery to deliver this preselected output by rotating the control means 116 relative to the barrel 126. A visual indication of the output selected may be indicated by means of aligning an index mark formed on the exterior of the control means 116 with a scale printed around the exterior of the barrel 126. The adjusted cautery barrel is then dropped into bag 32 in the previously described manner, the bag is sealed and the tip assembly is mounted to the adaptor means. Having selected the desired output, the operator moves the actuator means 124 through the bag to the second or "on" position to complete the circuit between the voltage source 122 and the heating tip assembly which has been mounted to the cautery causing the wire heater tip element 163 to heat up. Once heated, the heater element 163 may be touched to exposed wounds or cuts to clean and heal the wounds or remove sutures and the like. The control means 116 is disposed relative to the first conductor means 136 so that the position of the conductive strip 170 relative to the contact means 140 determines the voltage value applied to the heater element. In this manner the voltage limits of proper value are provided.

It is envisioned in all of the previously described embodiments that the outer bag which serves as a sterilizing covering for the cautery body can be removed and discarded and a new bag placed on the cautery body with subsequent tip assemblies being inserted into the cautery body for various cutting and cauterizing functions. Upon use these cutting tip assemblies can also be discarded so that the cautery bodies with their associated batteries can be reused as desired. It should be noted that in the uses of the described embodiments that the flexible bag covering allows the operating button 194 to be easily depressed thus completing the circuit in the disposable cauteries so that electricity is provided to the resistance tip thereby heating the tip to the desired degree necessary.

While the preferred embodiment of the invention has been disclosed, it is understood that the invention is not limited to such an embodiment since it may be otherwise embodied in the scope of the appended claims.

What is claimed is:

1. A portable cautery apparatus of the type utilizing a self-contained voltage source comprising a housing, a voltage source mounted in said housing and contained within said housing, control means adapted to control said voltage source moveably mounted to said housing in operative electrical engagement with said voltage source, adaptor means for providing a connection between said voltage source and a heater tip means, said adaptor means mounted to said housing and extending from said housing, said adaptor means comprising a member defining a blind bore and tubular first and second electrodes mounted in said member and substantially terminating at an end of said blind bore, said first electrode being electrically connected to said voltage source and said second electrode being electrically connected to said control means, said adaptor means member having a forward end formed with and terminating in a planar surface, a flexible sheath completely enclosing said housing to provide a contamination free environment for said housing, a disposable heater tip means adapted to be removably mounted to said adaptor means, said adaptor means being enclosed by said sheath and isolated from contact with said heater tip means in order to eliminate potential patient-to-patient contamination when said housing is utilized in consecutive surgical procedures, said heater tip means having a rear end which defines a planar surface, said heater tip means comprising a replaceable tip housing, tubular shaped third and fourth electrodes mounted inside said tip housing and extending therefrom, a heater element comprising a wire tip interconnected between ends of said third and fourth electrodes, the other ends of said third and fourth electrodes piercing said sheath and engaging said first and second electrodes of said adaptor means.

2. The cautery apparatus of claim 1 wherein said tip housing comprises a body defining a frustum-conical shaped portion and a male portion extending from said frustum-conical shaped portion, said male portion having a cross-sectional configuration substantially the same as the cross-sectional configuration of the blind bore of said adaptor means, said male portion being matingly received and mounted in said blind bore.

3. The cautery apparatus of claim 1 wherein said tip housing comprises a body portion having said third and fourth electrodes extending therefrom and a skirt portion adapted to seat adjacent said adaptor member and surrounding said adaptor member extending from said housing, said skirt portion having a cross-sectional configuration substantially the same as the cross-sectional configuration of said adaptor member.

4. The cautery assembly of claim 1 wherein the ends of said third and fourth electrodes have beveled cutting edges which facilitate insertion of said electrodes through said sheath to engage said first and second electrodes of said voltage source housing.

5. The cautery apparatus of claim 1 wherein said flexible sheath comprises a flexible plastic bag with sealing means at one end, said sealing means being adapted to close off the interior of said sheath from the external environment.

* * * * *